United States Patent [19]

Straube et al.

[11] Patent Number: 5,275,948
[45] Date of Patent: Jan. 4, 1994

[54] METHOD FOR REPROCESSING SCRAP RUBBER

[75] Inventors: Gunhild Straube; Eckhardt Straube; Willi Neumann; Helmut Rückauf; Ralf Forkmann, all of Halle-Neustadt; Martin Löffler, Berlin, all of Fed. Rep. of Germany

[73] Assignee: Hölzemann Metallverarbeitung GmbH, Rain am Lech, Fed. Rep. of Germany

[21] Appl. No.: 811,629

[22] Filed: Dec. 23, 1991

[30] Foreign Application Priority Data

Dec. 22, 1990 [DE] Fed. Rep. of Germany ....... 4042009

[51] Int. Cl.$^5$ .......................... C12M 1/10; C12R 1/07
[52] U.S. Cl. .......................... 435/262; 241/DIG. 31; 264/349; 264/DIG. 69; 264/37; 425/DIG. 46; 435/312
[58] Field of Search ...... 264/83, 349, DIG.; 210/619; 435/252.5, 262–; 521/40, 40.5, 41, 45, 41.5, 45.5; 425/DIG.

[56] References Cited

U.S. PATENT DOCUMENTS

| | | |
|---|---|---|
| 2,461,193 | 2/1949 | Banbury et al. ............... 521/45.5 |
| 2,686,754 | 8/1954 | Monod ............................ 435/312 |
| 2,975,103 | 3/1961 | Kirshenbaum .................. 435/832 |
| 3,540,589 | 11/1970 | Boris .............................. 435/312 |
| 4,161,464 | 7/1979 | Nicholas ........................ 521/41.5 |
| 4,530,763 | 7/1985 | Clyde et al. .................... 210/619 |
| 4,563,282 | 1/1986 | Wittmann et al. .............. 210/619 |
| 4,632,906 | 12/1986 | Kopacz ........................... 435/832 |
| 5,002,888 | 3/1991 | Kilbane, II ..................... 435/832 |

FOREIGN PATENT DOCUMENTS 211575 7/1984 Fed. Rep. of Germany ........ 521/41

Primary Examiner—Jeffery Thurlow
Assistant Examiner—Mathieu Vargot
Attorney, Agent, or Firm—Anderson Kill Olick & Oshinsky

[57] ABSTRACT

A method for reprocessing scrap rubber, which produces reclaimed rubber from comminuted scrap rubber after devulcanization, in a biotechnology-type of process, by holding the comminuted scrap rubber in a bacterial suspension of chemolithotropic microorganisms with a supply of air, until sulphur as an elementary sulphur and/or sulfuric acid is separated from the remaining replasticized reclaimed rubber. This biotechnological reprocessing obtains reclaimed rubber and sulphur in a simplified manner which products can be reused.

9 Claims, 1 Drawing Sheet

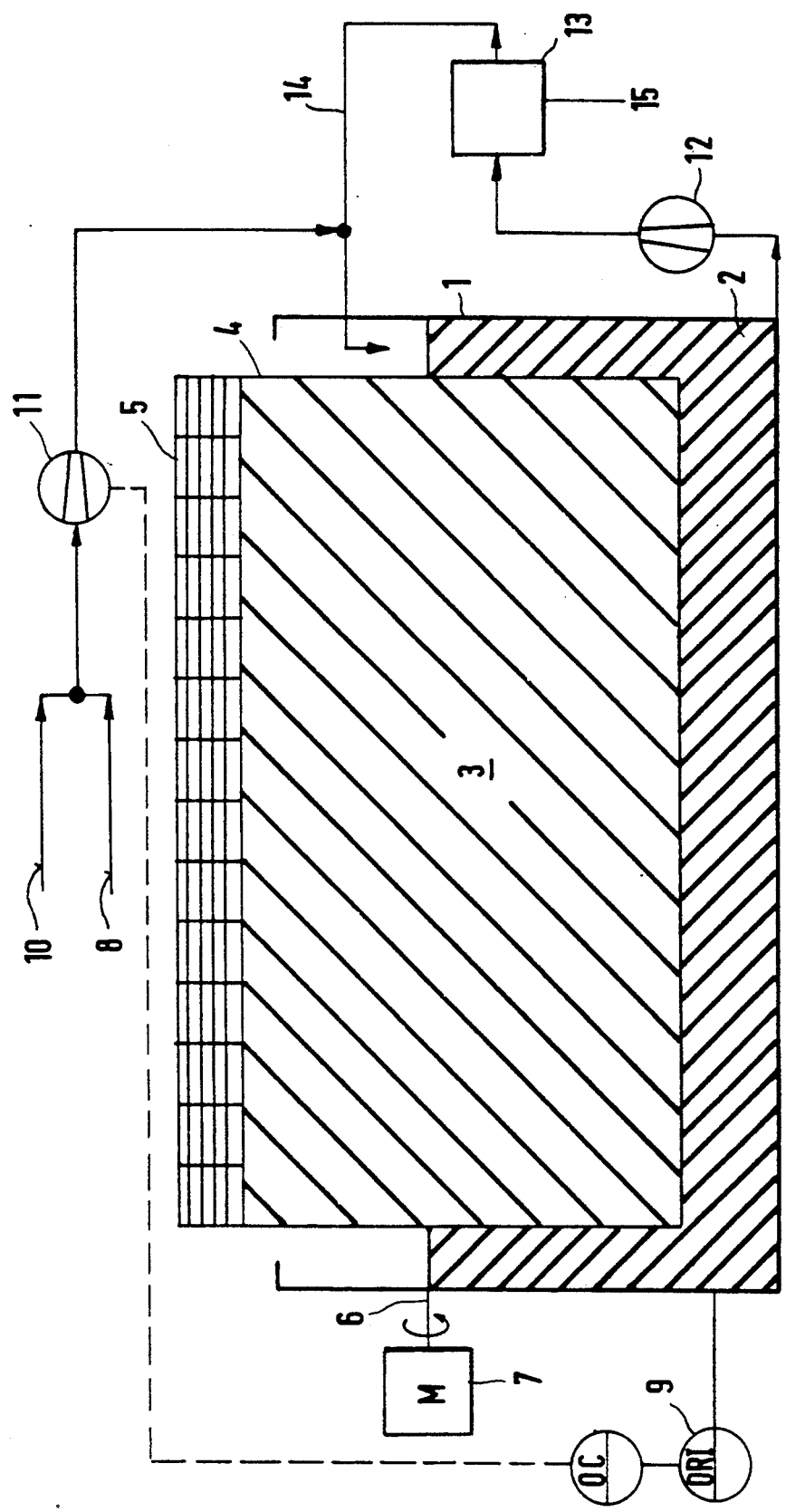

METHOD FOR REPROCESSING SCRAP RUBBER

BACKGROUND OF THE INVENTION

The present invention deals with a method for reprocessing scrap rubber where the scrap rubber contains sulphur and is comminuted, and the reclaimed rubber is produced from the comminuted scrap rubber by devulcanization.

The invention also deals with an apparatus for performing this method.

Every year several million tons of scrap rubber, especially old automobile tires, are rejected worldwide, which to date have been only insufficiently utilized as a secondary raw material. Due to the small share of rubber returned into the material circulation cycle by different reprocessing variants, for instance recapping of tires, there results a large accumulation of scrap tires in dumps, which require reprocessing. Hitherto, it was assumed that with scrap tires are naturally non-composable waste materials (DE 2638387).

To date the reprocessing of waste tires proceeded along three different process variants.

In the first variant, the scrap tires, after being granulated down to grain sizes of approximately 25 mm, are utilized as an additive for construction of bituminous road cover layers or strengtheners for athletic grounds. For this purpose the rubber granulate is mixed, in a mixer common in road construction, with cement, gravelly sand or sand, water and bonding improvement agents, and is used as a highly elastic intermediate layer, for instance in highway reconstruction or road rail construction (DE 2638387).

A second possibility of utilizing scrap tires as a secondary raw material consists in subjecting the scrap tires to a pyrolysis, in order to thereby obtain pyrolysis oil as initial material for chemical base materials or fuel oils for generation of heat energy and electrical energy from the use of the thermal energy of the incompletely burned gases by directly driving a gas turbine (DE 2724813). For this purpose the scrap tires are undercooled. The undercooled tires are as a rule fed to begin with to a coarse rubber crusher, where only the rubber of the tires is initially crushed in such a way that it can be detached from the bead wires. A twin rotor hammermill is for instance located downstream of the coarse rubber crusher, which knocks the basic components off from the carcass, which thereupon are sorted as to different grain sizes in a screening drum. Thereupon the rubber granulate is separated in magnetic separators and a screening installation from the remaining metal shares and cord fibers (DE 2724813). Subsequently the rubber ingredients are degassed at a temperature of approximately 500° C. The soot or carbon black produced therein can be used either as a product for further processing or as fuel oil. The incompletely burned gas produced as a result of the degassing process is used for directly driving a gas turbine and thus for energy generation.

The third possibility of utilizing scrap tires as secondary raw material consists in replasticizing the finely comminuted rubber granulate, for instance the rubber powder accumulating during the course of recapping old tires preferably in the extruder, and to reuse the granulate up to 20 shares or parts by weight in the tire breaker strip mixture when recapping old tires. Evident disadvantages of this method are the high installation and energy costs of the extruder or analogous installation as well as the use of chemicals, which cause a chain and/or cross-linkage decomposition or degradation and which remain entirely or partially in the replasticate. In addition only a relatively small part of the accumulating mass of scrap tires can be reused through regeneration.

SUMMARY OF THE INVENTION

It is an object of the present invention to create a method and an apparatus of the previously mentioned type, which operate according to the principles of biotechnology. Pursuant to this object, in the inventive method the comminuted scrap rubber is held in a bacterial suspension of chemolithotropic microorganisms with the addition of air, until the sulphur is partially or completely separated from the remaining replasticized reclaimed rubber in the form of elementary sulphur and/or sulfuric acid.

In the method of the invention the sulphur in the scrap rubber is partially or completely split off and this sulphur is collected and fed to a reutilization process. The reclaimed rubber is also fed to a reutilization process and can be reutilized also if the sulphur has not been completely split off. Chemolithotropic bacteria, for instance the species Thiobacillus or sulphur bacteria, are able in the presence of air (oxygen and carbon) to split the sulfide bridges of the rubber and thus to replastisize the rubber material, whereby the reprocessing of the carbon chains split off from the sulphur and a reutilization of the sulphur compounds released by the bacteria is made possible. Herein elementary sulphur and/or sulfuric acid are produced through oxidation by the bacteria as a function of the supplied air. The method of the invention works at a lower cost, without chemicals, faster and with an improved output, as compared to conventional methods. Zinc oxide and other metal oxides are split off together with the sulphur and are transposed into the suspension. Other additive materials of the scrap rubber, for instance carbon black, bitumens, and stearic acid, essentially remain in the reclaimed rubber. The sulphur compounds containing oxygen produced by oxidation are concentrated and neutralized.

It is especially desirable and advantageous, if the splitting off of sulphur covers only a superficial layer of the scrap rubber particles and if the core of the particles remain in the state of scrap rubber. The thickness of the superficial layer amounts for instance to a few $\mu$m. This regenerated material can in certain circumstances be processed further in an improved and adapted manner.

It is especially desirable and advantageous, if the chemolithotropic bacteria are Thiobacillus ferrooxidans, Thiobacillus thioxidans and/or Thiobacillus thioparus. These types of bacteria of the species Thiobacillus are easy to handle and to keep effective.

It is also especially desirable and advantageous, if when using Thiobacillus ferrooxidans and Thiobacillus thiooxidans, the pH-value of the bacterial suspension is kept within 1 to 4, preferably within 1.5 to 2.5. When using Thiobacillus thioparus, the pH-values are to be held within 4 to 7, preferably 5.5 to 7. In these ranges of pH-values the chemolithotropic microorganisms are more effective in splitting-off sulphur. The pH-value is continuously measured by a measuring arrangement. The pH-value adjustment occurs for instance by regulated addition of a nutritive solution and/or of a chemical, for instance NaOH.

The split-off sulphur goes over into the bacterial suspension. It is therefore especially desirable and advantageous if the elementary sulphur and/or the sulfuric acid are split off together with the bacterial suspension and are thereupon separated from the bacterial suspension. This is a simple way to present the split-off sulphur itself.

The apparatus for performing the inventive method can be formed of, for instance, a waste dump reactor, where the bacterial suspension is sprayed from the top over the comminuted scrap rubber lying in a shallow basin, where the scrap rubber is exposed to air.

In a preferred embodiment of the invention, a basin is provided for receiving the bacterial suspension up to a surface level and a rotationally supported screening drum is assigned to the basin, which drum partially protrudes above the surface level and partially plunges below the surface level.

Here also no special air supply is provided and the oxygen in the air is used. This apparatus works in a more controlled manner and faster than the waste dump reactor. The scrap rubber particles are agitated or moved by the rotating drum, they are mixed and repeatedly exposed to the air as well as being submerged into the bacterial suspension.

Another preferred embodiment of the invention including providing a rotationally supported closed drum, which comprises radially extending and compartment-forming walls for receiving the comminuted scrap rubber and the bacterial suspension. While the screening drum as a rule is utilized at grain sizes exceeding 80 µm, as a rule grain sizes below 80 µm are used in the present closed drum. As a rule and in adaptation to the chemolithotropic microorganisms the comminuted scrap rubber has a particle size of 50 µm up to 1000 µm preferably 50 µm to 350 µm.

The comminution of the scrap rubber into a granulate is performed by known processes, as for instance through cooling by liquefied nitrogen (DE 2803859; DE 2145728) or solidified carbon dioxide (DE 2638387) and subsequent comminution in conventional grinding arrangements, as for instance hammermills, up to grain sizes of 1 to 15 mm, preferably of 5 to 7 mm. A reprocessing of the rubber powder accumulating when recapping old tires is possible also without a preceding comminution.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

The drawing shows diagrammatically and partially in section an apparatus pursuant to the present invention for reprocessing of scrap rubber.

DETAILED DESCRIPTION OF THE PREFERRED EMBODIMENTS

As seen in the drawing, granulate from scrap rubber is supplied after comminution to a trough-like container 1 containing a bacterial suspension 2 with the simultaneous presence of oxygen. The apparatus is selectively laid out in such a way that either a batch-wise or however a quasi-continuous or continuous input and output of the fresh, meaning of the rubber material to be reprocessed or of the reprocessed rubber granulate containing little sulphur, is possible.

It is provided in the present apparatus, that the rubber granulate is transposed into at least one drum basket 4 consisting of stainless steel wire mesh, and is charged to the drum basket 4 at the upper portion of the container, for instance by means of a hoisting device. The at least one drum baskets is provided with a loading and unloading or charging and discharging flap 5 and is supported or fastened on a shaft 6 so that a continuous and uniform rotation of the drum basket 4 is assured by a motor drive 7 coupled to the shaft 6. After the rubber material has been reprocessed, the drum basket 4 is again removed from the container 1 and the rubber material containing little sulphur or the reclaimed rubber are supplied to a separate unit for further processing. Due to the continuous rotation of the drum basket 4 filled with rubber granulate 3, which plunges by approximately 30 to 40 quantity shares, preferably 30 to 35 quantity shares of the charged rubber granulate into the bacterial suspension, the rubber granulate 3 is continuously bathed by the bacterial suspension 2 in the container 1.

The container 1 is for instance shaped as a basin, through whose liquid surface level the drum basket 4 rotates, so that an adequate contact between the bacterial suspension 2 and the rubber granulate 3 is assured. Furthermore, an enlargement of the material transition surface between the liquid or the suspension 3 and the air is achieved at the liquid surface level because of the rotation of the drum basket 4, so that it is possible to do without a separate oxygen supply for gas absorption by the suspension.

A defined quantity of nutritive solution and trace elements is added through a supply line 8 to the bacteria suspension 2 continuously or at specific time intervals, for instance daily. The pH-value of the bacterial suspension is continuously measured by a permanently operating pH-measuring device 9 and is always adjusted to the pH-value which is respectively optimum for the reprocessing. The regulation of the pH-value can be realized by addition of the necessary nutritive solution through the supply line 8 and/or by addition of chemicals through a supply line 10 and by a following downstream supply arrangement 11. For instance, waste dump reactors can be used as an additional embodiment form of the bio-reactor, such as are used in leaching processes of low-grade ores, described for instance in Torma, A. E. "Current Standing Heap, Dump, In-Situ Leaching Technology of Copper"; Metall 38 (1984) Page 1044–1047.

With a limited oxygen supply for the bacteria there occurs principally an oxidation of the sulphur bound in the rubber into elementary sulphur. A portion of the bacterial suspension 2, together with the sulphur produced by the bacteria, is drawn off at the bottom of the container 1 by a pump 12 and is supplied to a separation stage 13, preferably a hydrocyclone or a filtering unit, this for separating the sulphur. After the sulphur has been separated in the separation stage 13, the suspension devoid of sulphur is again supplied into the container 1 through a line 14.

While the invention has been illustrated and described as embodied in a method and apparatus for reprocessing scrap rubber, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

1. A method for reprocessing scrap rubber that contains sulphur in the form of sulfide bridges, comprising the steps of:

comminuting the scrap rubber into scrap rubber particles;

devulcanizing the comminuted scrap rubber by splitting the sulfide bridges to produce reclaimed rubber by holding the said particles in a bacterial suspension of chemolithotropic microorganisms with a supply of air, until the sulphur is at least partially separated as at least one of elementary sulphur and sulphuric acid from remaining replacticized reclaimed rubber and until a separation of sulphur by splitting the sulfide bridges covers only a superficial layer of the scrap rubber particles so that a core of the particles remains in a state of scrap rubber.

2. A method according to claim 1, wherein the chemolithotropic microorganism is selected from the group consisting of Thiobacillus ferrooxidans, Thiobacillus thiooxidans and Thiobacillus thioparus.

3. A method according to claim 2, wherein when using at least one of Thiobacillus ferrooxidans and Thiobacillus thiooxidans, the bacterial suspension has a pH value that is held at 1 to 4.

4. A method according to claim 3, wherein the pH level is held at 1.5 to 2.5.

5. A method according to claim 2, wherein when using Thiobacillus thioparus, the pH-value of the bacterial suspension is held at 4 to 7.

6. A method according to claim 5, wherein the pH level is held at 5.5 to 7.

7. A method according to claim 1, wherein the comminuting step includes comminuting the scrap rubber to a particle size of 15 $\mu$m up to 1000 $\mu$m.

8. A method according to claim 1, wherein the scrap rubber is comminuted to a particle size of 50 $\mu$m to 350 $\mu$m.

9. The method according to claim 1, wherein the scrap rubber is comminuted to a particle size of 50 $\mu$m to 1,000 $\mu$m.

* * * * *

UNITED STATES PATENT AND TRADEMARK OFFICE
CERTIFICATE OF CORRECTION

PATENT NO. : 5,275,948
DATED : January 4, 1994
INVENTOR(S) : Gunild Straube, et al.

It is certified that error appears in the above—identified patent and that said Letters Patent is hereby corrected as shown below:

On the title page, insert the following:

[75] Inventors:   Gunhild Straube; <u>Ekkehard</u> Straube;
Willi Neumann; Helmut Rückauf;
Ralf Forkmann, all of Halle-Neustadt;
Martin Löffler, Berlin, all of Fed. Rep.
of Germany Signed and Sealed this Fifteenth Day of April, 1997

Attest:

BRUCE LEHMAN

Attesting Officer     Commissioner of Patents and Trademarks